(12) United States Patent
Nakamoto et al.

(10) Patent No.: US 8,124,137 B2
(45) Date of Patent: Feb. 28, 2012

(54) COMPOSITION FOR PREVENTION AND/OR TREATMENT OF TUMORS CONTAINING ACACIA BARK DERIVATIVE

(75) Inventors: Yusho Nakamoto, Hatsukaichi (JP); Keiko Ono, Hatsukaichi (JP)

(73) Assignee: Mimozax Co., Ltd., Hatsukaichi-shi (JP)

( * ) Notice: Subject to any disclaimer, the term of this patent is extended or adjusted under 35 U.S.C. 154(b) by 100 days.

(21) Appl. No.: 12/376,895

(22) PCT Filed: Aug. 10, 2006

(86) PCT No.: PCT/JP2006/315865
§ 371 (c)(1),
(2), (4) Date: Feb. 9, 2009

(87) PCT Pub. No.: WO2008/018140
PCT Pub. Date: Feb. 14, 2008

(65) Prior Publication Data
US 2010/0178370 A1    Jul. 15, 2010

(51) Int. Cl.
*A61K 36/00* (2006.01)
(52) U.S. Cl. .................................. 424/725; 424/775
(58) Field of Classification Search .................. None
See application file for complete search history.

(56) References Cited

U.S. PATENT DOCUMENTS

| | | | |
|---|---|---|---|
| 5,629,338 | A | 5/1997 | Okuda et al. |
| 6,290,993 | B1 | 9/2001 | Anderson et al. |
| 6,294,190 | B1 | 9/2001 | Nakahara et al. |
| 7,514,469 | B2 | 4/2009 | Jia |
| 2003/0180402 | A1 | 9/2003 | Jia et al. |
| 2003/0232099 | A1 | 12/2003 | Pan et al. |
| 2004/0186062 | A1 | 9/2004 | Burnett et al. |
| 2005/0058722 | A1* | 3/2005 | Managoli ............. 424/623 |
| 2005/0095332 | A1 | 5/2005 | Stanley |
| 2006/0204599 | A1 | 9/2006 | Wheat |
| 2008/0124415 | A1 | 5/2008 | Tanaka et al. |

FOREIGN PATENT DOCUMENTS

| | | |
|---|---|---|
| CN | 1753681 A | 3/2006 |
| FR | 2 710 533 A1 | 4/1995 |
| JP | 64-025726 U | 2/1989 |
| JP | 3-287507 A | 12/1991 |
| JP | 6-065074 A | 3/1994 |
| JP | 7-138178 A | 5/1995 |
| JP | 7-300422 A | 11/1995 |
| JP | 8-259557 A | 10/1996 |
| JP | 9-291039 A | 11/1997 |
| JP | 10025238 A * | 1/1998 |
| JP | 11-005975 A | 1/1999 |
| JP | 11-180888 A | 7/1999 |
| JP | 2000-044472 A | 2/2000 |
| JP | 2000-073056 A | 3/2000 |
| JP | 2001-064172 | 3/2001 |
| JP | 2001-098264 A | 4/2001 |
| JP | 2002-010753 A | 1/2002 |
| JP | 2002-051735 A | 2/2002 |
| JP | 2002-275076 A | 9/2002 |
| JP | 2003-519092 A | 6/2003 |
| JP | 2003-313138 A | 11/2003 |
| JP | 2003-342185 A | 12/2003 |
| JP | 2004-008215 A | 1/2004 |
| JP | 2004-024054 A | 1/2004 |
| JP | 2004-051513 A | 2/2004 |
| JP | 2004-075579 A | 3/2004 |
| JP | 2004-091464 A | 3/2004 |
| JP | 2004-217559 A | 8/2004 |
| JP | 2004-300117 A | 10/2004 |
| JP | 2004532811 T | 10/2004 |
| JP | 2004-323362 A | 11/2004 |
| JP | 2004352639 A | 12/2004 |
| JP | 2005-068081 | 3/2005 |
| JP | 2005-521715 A | 7/2005 |
| JP | 2005-239559 A | 9/2005 |
| JP | 2005-529898 A | 10/2005 |
| JP | 2006-232781 A | 9/2006 |
| JP | 2006-232782 A | 9/2006 |
| WO | WO-03/082312 A1 | 10/2003 |
| WO | 03-092599 A2 | 11/2003 |
| WO | 2005-020932 A2 | 3/2005 |
| WO | 2006-003909 A | 1/2006 |

OTHER PUBLICATIONS

"Introduction" of Cancer from Merck Manual, pp. 1-2, accessed on Dec. 4, 2010.*
Tomatis, Environmental cancer risk factors, Acta oncologica (Stockholm, Sweden), (1988) vol. 27, No. 5, pp. 465-472.*
Kronborg, Population screening for colorectal cancer, the goals and means, Annals of medicine, (Oct. 1991) vol. 23, No. 4, pp. 373-379.*
Garewal et al, Clinical experience with the micronucleus assay, Journal of Cellular Biochemistry, (1993) vol. 52, No. SUPPL. 17 F, pp. 206-212.*
Cheng et al, A novel approach to microcalcification detection using fuzzy logic technique, IEEE transactions on medical imaging, (Jun. 1998) vol. 17, No. 3, pp. 442-450.*
Granziero et al. Adoptive immunotherapy prevents prostate cancer in a transgenic animal model, Eur. J. Immunol. 1999, 29:1127-1138.*
Byers, T, What can randomized controlled trials tellus about nutrition and cancer prevention, CA Journal, vol. 49, No. 6, Nov./Dec. 1999.*
"Risk factor for cancer" from Merck Manual, pp. 1-4, accessed on Apr. 14, 2009.*
De Oliveira at al, Antitumor activity of condensed flavanols, Academia Brasileira De Ciencias Rio de Janeiro, 1972; 44 (1): 41-4.*
Roux, the biogenesis of bark and heartwood tannis of some *Acacia* spp, and their taxonomic significance, South African Journal of Science, 1962; 58 (12): 389-392.*
Prakash et al, Characterization of tannin from Indian wattle (*Acacia mearnsii*) bark, Indian Journal of Forestry, 14 (4): 299-302, 1991.*
Ohara "Chemical Properties and Application Development of Bark Tannin", APAST, vol. 13, No. 1 (Jan. 2003) pp. 7-11 (and English Translation, pp. 1-10).
De Oloveira et al., "Antirumor Activity of Condensed Flavanols", Anais da Academia Brasileira de Ciencias, 1972, vol. 44, No. 1, pp. 41-44.

(Continued)

*Primary Examiner* — Qiuwen Mi
(74) *Attorney, Agent, or Firm* — Birch, Stewart, Kolasch & Birch, LLP (57) ABSTRACT

It is intended to provide a composition which is useful in preventing or treating a tumor. The composition is a composition for the prevention and/or treatment of a tumor, containing an *acacia* bark derivative.

9 Claims, 2 Drawing Sheets

OTHER PUBLICATIONS

Ohara et al., "Condensed Tannins from *Acacia mearnsii* and Their Biological Activities", Mokuzai Gakkaishi, 1994, vol. 40, No. 12, pp. 1363-1374.

Ohara et al., "Juhi Tannin no Kagaku Tokusei to Yoto Kaihatsu", APAST, 2003, vol. 13, No. 1, pp. 7-11.

Takagi et al., "Tyrosinase Inhibitory Activity of Proanthocyanidins from Woody Plants", J. Wood Sci, 2003, vol. 49, No. 5, pp. 461-465.

Botha et al., "Condensed tannins: direct synthesis, structure, and absolute configuration of four biflavonoids from black wattle bark ('mimosa') extract," J Chem Soc, Chem Commun, 1978, vol. 16, pp. 700-702.

Chang et al., "Antioxidant activity of extracts from *Acacia confusa* bark and heartwood," J Agric Food Chem, Jul. 2001, vol. 49, No. 7, pp. 3420-3424.

Duan et al., "Condensed tannins from steamed *Acacia mearnsii* bark," Holzforschung, May 2005, vol. 59, No. 3, pp. 289-294.

Fragrance Journal, 1995, 23(10), pp. 96-102 (with English language abstract).

Haridas et al., "Avicins: triterpenoid saponins from *Acacia victoriae* (Bentham) induce apoptosis by mitochondrial perturbation," PNAS, May 8, 2001, vol. 98, No. 10, pp. 5821-5826.

Ishida et al., "Solid sampling technique for direct detection of condensed tannins in bark by matrix-assisted laser desorption/ionization mass spectrometry," Rapid Commun Mass Spectrom, 2005, vol. 19, No. 5, pp. 706-710.

Japanese Office Action issued in Japanese Patent Application No. 2005-132746 on Aug. 2, 2011.

Liu et al., "Antidiabetic effect of Pycnogenol French maritime pine bark extract in patients with diabetes type II," Life Sci, Oct. 8, 2004, vol. 75, No. 21, pp. 2505-2513.

Orwa et al., "*Acacia mearnsii*, black wattle", Agroforestry Database 4.0 (2009) pp. 1-5.

Properties, Composition, Reactions and Industrial Applications of Mimosa Extract, African Territories Wattle Industry Fund Limited, Jan. 1980, London, England.

Seigler, "Phytochemistry of *Acacia-sensu* lato," Biochemical Systematics and Ecology, 2003, vol. 31, No. 8, pp. 845-873.

Taguchi et al., "Evaluation of antipruritic effect of apple polyphenols using a new animal model of pruritus." J. Tokyo Med. Univ., Feb. 15, 2002, vol. 60, No. 2, pp. 123-129.

U.S. Office Action issued in U.S. Appl. No. 12/376,905 on Dec. 20, 2010.

U.S. Office Action issued in U.S. Appl. No. 12/376,905 on Jan. 3, 2011.

U.S. Office Action issued in U.S. Appl. No. 12/376,895 on Jan. 6, 2011.

U.S. Office Action issued in U.S. Appl. No. 12/376,895 on May 2, 2011.

U.S. Office Action issued in U.S. Appl. No. 12/376,895 on Nov. 2, 2010.

U.S. Office Action issued in U.S. Appl. No. 12/376,902 on Jan. 3, 2011.

U.S. Office Action issued in U.S. Appl. No. 12/376,902 on Jun. 15, 2011.

U.S. Office Action issued in U.S. Appl. No. 12/376,902 on Oct. 20, 2010.

U.S. Office Action issued in U.S. Appl. No. 12/376,904 on Aug. 31, 2010.

U.S. Office Action issued in U.S. Appl. No. 12/376,904 on Feb. 16, 2011.

U.S. Office Action issued in U.S. Appl. No. 12/376,904 on Jun. 17, 2011.

U.S. Office Action issued in U.S. Appl. No. 12/376,939 on Jan. 10, 2011.

U.S. Office Action issued in U.S. Appl. No. 12/376,939 on Jul. 21, 2011.

U.S. Office Action issued in U.S. Appl. No. 12/376,939 on Oct. 7, 2010.

Wassel et al., "Phytochemical examination and biological studies of *Acacia nilotica* L. Willd and *Acacia farnesiana* L. Willd growing in Egypt," Egyptian Journal of Pharmaceutical Sciences, 1992, vol. 33, Nos. 1-2, pp. 327-340.

Japanese Office Action issued in JP 2005-132745 on Sep. 13, 2011, with English translation.

Kaur, "Antimutagenicity of ether and ethyl acetate fractionsn of acacia nilotica in Ames assay", Breast, vol. 12, No. Supplement, (2003) p. s47.

* cited by examiner

\#: Indicates P < 0.05 versus Control 1 group.
*: Indicates P < 0.05 versus Control 3 group.

COMPOSITION FOR PREVENTION AND/OR TREATMENT OF TUMORS CONTAINING ACACIA BARK DERIVATIVE

TECHNICAL FIELD

The present invention relates to a composition derived from a tree belonging to the genus *Acacia* for preventing and/or treating a tumor, and to uses of this composition as a food, an animal feed material and a medicine.

BACKGROUND ART

Although deaths caused by infections have decreased dramatically in Japan through the improvement in public health and the discovery of antibiotics and the like following the Second World War, the incidences of lifestyle diseases and particularly cancer have continued to increase in their place, with cancer having become the leading cause of death amongst Japanese in 1981. At present, about one out of every three persons dies of cancer. In addition, cancer is rapidly proliferating not only in Japan but in other countries as well, and is a disease that can be considered to be a common enemy of all persons.

Thus, the development of methods for preventing or treating tumors including cancer is considered to be an important and critical issue.

In actuality, although various anticancer drugs have been developed and are currently in use as therapeutic drugs, these have numerous problems, including the occurrence of serious adverse side effects.

With respect to *acacia*, *acacia* honey is known, and tannin which is extracted from bark thereof is known to be able to be used as a tanning agent or wood adhesive, while more recently, extracts of genus *Acacia* have been disclosed to have selective inhibitory effects on COX-2 (Patent Document 1), and bark of genus *Acacia* has been disclosed to have active oxygen elimination effects (Patent Document 2) and skin whitening effects due to the effect of inhibiting tyrosinase activity (Patent Document 3). However, *acacia* bark and polyphenols derived from *acacia* bark have heretofore not been confirmed to have an antitumor action.
[Patent Document 1] JP 2004-532811 A
[Patent Document 2] JP 2004-352639 A
[Patent Document 3] JP 10-025238 A

DISCLOSURE OF THE INVENTION

Problems to be Solved by the Invention

The object of the present invention is to provide an extremely safe composition that is useful for the prevention and/or treatment of tumors.

Means for Solving the Problems

As a result of conducting extensive studies to solve the above problems, the inventors of the present invention found that an *acacia* bark derivative has an excellent antitumor activity to be useful for the prevention or treatment of tumors, thereby leading to the completion of the present invention.

Namely, the present invention relates to a composition for the prevention and/or treatment of tumors, containing an *acacia* bark derivative(s).

In addition, the present invention also relates to a method for preventing or treating tumors using an *acacia* bark derivative(s).

Moreover, the present invention relates to a method for using an *acacia* bark derivative(s) for producing a composition for preventing or treating tumors.

Effects of the Invention

The composition of the present invention has an antitumor activity, and in particular, an excellent anti-malignant tumor activity.

In addition, the composition of the present invention is very safe and has less potential for adverse side effects and the like even if taken for a long period of time.

BEST MODE FOR CARRYING OUT THE INVENTION

There are no particular limitations on the *acacia* bark derivative able to be used in the present invention provided that it is obtained by using as a raw material bark of a tree belonging to the genus *Acacia* (the tree is referred to as "*acacia*" or "genus *Acacia*" hereinafter), examples of which derivatives include a strip and a powder of *acacia* bark, and a suspension thereof, an extract such as a liquid extract, a concentrated liquid extract and a powdered extract of *acacia* bark, and a purified product obtained by purifying these extracts. The extract of *acacia* bark and particularly *acacia* bark polyphenols are preferable for giving an excellent antitumor activity.

In the present invention, only a single form of these *acacia* bark derivatives may be used, or alternatively two or more forms thereof may be used in combination.

Although there are no particular limitations on *acacia* able to be used in the present invention so long as it is a tree belonging to the genus *Acacia*, with respect to obtaining an *acacia* bark derivative having an excellent antitumor action, bark of the genus *Acacia* selected from the group consisting of scientific name: *Acacia mearnsii* De Wild. (generic name: black wattle), scientific name: *Acacia mangium* Willd. (generic name: *acacia mangium*), scientific name: *Acacia dealbata* Link, scientific name: *Acacia decurrens* Willd. and scientific name: *Acacia pycnantha* Benth. are preferable, while *Acacia mearnsii* De Wild. and *Acacia mangium* Willd. are particularly preferable.

In the present invention, only a single form of these *acacia* bark may be used, or alternatively two or more forms thereof may be used in combination.

The aforementioned *acacia* bark can normally be obtained by cutting down an *acacia* tree, pealing off only bark and then drying the bark more preferably by sun-drying.

Bark of *acacia* is comprised of an outer bark and a somewhat fibrous inner bark, and when dried to a moisture content of about 20% or less, can be easily finely pulverized with a size reduction mill such as a hammer mill. In the present invention, both the outer bark and inner bark of the genus *Acacia* may be used together or either one may be used alone as the *acacia* bark.

The aforementioned strip of *acacia* bark can be obtained in accordance with commonly used methods by pulverizing the *acacia* bark to a suitable size.

In addition, although the aforementioned powder of *acacia* bark can be obtained by pulverizing the *acacia* bark into a powder in accordance with commonly used methods, in particular, the particle diameter of the resulting powder is preferably 100 μm or less and particularly preferably 50 to 70 μm. Powder fractionation can be carried out by pulverizing the bark dried to a moisture content of 20% or less to a suitable size such as a particle diameter of about 1.6 mm or less, and then classifying the resulting powder with a vibrating screen or the like to obtain the required powder.

The aforementioned extract of *acacia* bark can be obtained by extraction from the *acacia* bark in accordance with commonly used methods. In order to obtain an extract of *acacia* bark having an excellent antitumor activity, it is preferably extracted from the *acacia* bark with an alcohol or a polar solvent.

Ethanol, etc. can be used as the alcohol, and water, etc. can be used as the polar solvent, and these solvents may be used singly or in combination of two or more kinds as necessary. A mixed solvent of water and the alcohol such as ethyl alcohol is particularly preferable for production of an excellent antitumor activity.

Moreover, the extraction procedure may be carried out a number of times using the same or different solvents.

An extract having an excellent antitumor activity can be obtained from the *acacia* bark by extraction with water or hot water, and then further extraction from the resulting extract with ethanol.

Although the extraction is carried out by adding the solvent to a strip, a powder or the like of the *acacia* bark followed by stirring as necessary, there are no particular limitations on temperature, time or solid-liquid ratio. In the case of using water as the solvent, the extraction may also be carried out with hot water. The resulting liquid extract may be freeze-dried or spray-dried directly, or may be freeze-dried or spray-dried after concentrating under reduced pressure. The resulting extract can be in various forms, such as a liquid extract, solution, powder, concentrate or paste, and can be used in a wide range of forms as necessary.

Moreover, the *acacia* bark extract of the present invention obtained in any of these forms can be used directly for the prevention or treatment of a tumor, or a purified product obtained by purifying the extract as necessary can also be used as an antitumor active ingredient.

In the present invention, ingredients contained in bark of the genus *Acacia* are also examples of the *acacia* bark derivatives. Examples of such ingredients are the *acacia* bark polyphenols. The *acacia* bark polyphenols are particularly preferable ingredients since they produce excellent antitumor activity.

The *acacia* bark polyphenols of the present invention refer to a type of condensed tannins in the form of polymers in which flavanols having as a basic skeleton flavan-3-ol such as (−)-fisetinidol, (−)-robinetinidol, (+)-catechin and (+)-gallocatechin are linked by C4-C8 or C4-C6 bonds. Here, the molecular weights of such condensed tannins are preferably 300 to 3000 and particularly preferably 500 to 3000. The *acacia* bark polyphenols used in the present invention can be obtained by extraction from the powder, etc. of the *acacia* bark with hot water as previously described.

In addition, examples of commercially available *acacia* bark polyphenols include MIMOSA ME POWDER, MIMOSA MS POWDER, MIMOSA GS POWDER, MIMOSA FS POWDER, MIMOSA WS POWDER, MIMOSA RG POWDER, MIMOSA RN POWDER, MIMOSA DK POWDER, MIMOSA AL POWDER, MIMOSA CR POWDER and GOLDEN MIMOSA POWDER (all registered trademarks) which are manufactured by Mimosa Central Co-operative Ltd., and the like.

Although the composition of the present invention may be the *acacia* bark derivative(s) such as the *acacia* bark, the extract(s) thereof, the purified product(s) thereof or the *acacia* bark polyphenol(s) per se, it may also contain other substance(s) having an antitumor activity, such as a substance useful in the prevention and/or treatment of tumors, examples of which include shark ointment, medicinal ginseng, caterpillar fungus, chitin, chitosan, agarisk, maitake, hardwood trunk rot, mekabu seaweed, mozuku seaweed and gulfweed.

Although the composition of the present invention may be the *acacia* bark derivative(s) such as the *acacia* bark, the extract(s) thereof, the purified product(s) thereof or the *acacia* bark polyphenol(s) per se, it may contain vehicles, sweeteners, sour flavorings, thickeners, fragrances, pigments, emulsifiers, and other additives or materials which are ordinarily used in drugs or foods, so long as they do not undermine the effects of the present invention.

Examples of tumors able to be prevented or treated with the composition of the present invention include benign or malignant tumors (cancers). Examples of benign tumors include pigmented nevus, dysplastic nevus, skin tag, lipoma, lymphangioma, seborrheic keratosis, dermatofibroma, keratoacanthoma, soft tissue tumors such as keloids, or polyps such as colorectal polyps or vocal cord polyps, while examples of malignant tumors include hematopoietic malignant tumors such as acute or chronic leukemia, malignant lymphoma, myeloma or macroglobulinemia; solid tumors such as a brain tumor, cancers of the head and neck (including laryngeal cancer, pharyngeal cancer and cancer of the tongue, etc.), breast cancer, lung cancer, esophageal cancer, gastric cancer, colorectal cancer, liver cancer, gallbladder and bile duct cancer, pancreatic cancer, renal cancer, adrenocortical cancer, bladder cancer, prostate cancer, testicular tumor, ovarian cancer, uterine cancer, choriocarcinoma, thyroid cancer, malignant cartinoid tumor, skin cancer, malignant melanoma, osteosarcoma, chondrosarcoma, soft tissue sarcoma, rhabdomyosarcoma, leiomyosarcoma, fibrosarcoma, liposarcoma or hemangiosarcoma; or cancers derived there from or associated therewith.

The composition of the invention of the present application is particularly useful for the prevention or treatment of leukemia, breast cancer, gastric cancer, colorectal cancer, liver cancer, renal cancer and hemangiosarcoma, and especially for the prevention or treatment of leukemia and breast cancer.

Furthermore, in the present invention, treatment includes shrinking or curing a tumor as well as inhibiting growth, metastasis or exacerbation of a tumor.

There are no particular limitations on an ingested amount of the composition according to the present invention, and the ingested amount can be suitably selected depending on the dosage form as well as the age, body weight and symptoms of an ingesting person such as a user or patient, or an ingesting animal. For example, it is desired that the ingesting person or ingesting animal orally ingests an amount of the *acacia* bark polyphenol(s) ranging from 0.001 to 1 g, preferably from 0.001 to 0.5 g and more preferably from 0.005 to 0.1 g per 1 kg of body weight per day in terms of the amount of active ingredient, since it produces an excellent antitumor activity.

The duration of ingestion can be arbitrarily determined depending on the age and symptoms of the user or patient.

The composition according to the present invention can be used as a food or an animal feed material, for example, as a health food, a functional food, a health supplement food, a food for specified health use, a beauty food or a nutritional supplement food (supplement). For example, these foods or animal feed material may also be in the form of a beverage such as tea or juice; ice cream, jelly, candy, chocolate or chewing gum, etc. In addition, they may also be in the form of liquids, powders, granules, capsules or tablets. Here, animals fed by the animal feed material include all animals requiring the prevention or treatment of tumors, including pets, livestock or animals bred at zoos, etc.

In addition, the composition according to the present invention can be used as a medicine or a guasi-drug. Although the medicine or guasi-drug can be administered, for example, orally in the form of powders, tablets, coated tablets, sugar coated pills, hard or soft gelatin capsules, liquids, emulsions or suspensions, they can also be administered rectally such as in the form of suppositories, topically or percutaneously such as in the form of ointments, creams, gels or liquids, or parenterally such as in the form of liquids for injection. However, they are preferably administered orally.

EXAMPLES

Although the following provides a more detailed explanation of the present invention through production examples, test examples and formulation examples thereof, the present invention is not limited thereto. In particular, although the following examples are indicated without making a distinction between the outer bark and inner bark of the *acacia* bark of the present invention, the outer bark can be separated from the inner bark and each can also be used, separately.

In the following production examples, test examples and the like, each *acacia* of the present invention is indicated with numbers shown in parentheses after each scientific name. For example, *acacia* known by the scientific name of *Acacia mearnsii* De Wild. is indicated as *Acacia* No. 1.

Scientific name: *Acacia mearnsii* De Wild. (No. 1), scientific name: *Acacia mangium* Willd. (No. 2), scientific name: *Acacia dealbata* Link (No. 3), scientific name: *Acacia decurrens* Willd. (No. 4), scientific name: *Acacia pycnantha* Benth. (No. 5).

In addition, percentages (%) refer to percent by weight (wt %) unless specifically indicated otherwise.

Production Example 1

*Acacia* Bark Powder

Bark of *Acacia* No. 1 was dried to a moisture content of 20% or less and after pulverizing the dried bark in a hammer mill to a powder having a particle diameter of 1.6 mm or less (the powder passing through a 10 mesh Tyler screen), the powder was further classified with a vibrating screen to obtain a fine powder having a particle diameter of 63 µm or less (passing through a 250 mesh screen).

Fine powders each having a particle diameter of 63 µm or less were similarly obtained by pulverizing bark of the remaining four types of *acacia* namely *Acacia* No. 2 to *Acacia* No. 5. Although there were some differences in the efficiency by which the fine powder passed through the 250 mesh screen depending on the type, all of the target fine powders were able to be obtained.

Production Example 2

*Acacia* Bark Extract

Bark of each *Acacia* No. 1 to 5 of the present invention was dried to a moisture content of 20% or less and after pulverizing the dried bark in a hammer mill to a powder having a particle diameter of 1.6 mm or less, five times the amount of hot water were added to 100 g of the dried pulverized bark followed by extraction for 15 minutes after boiling, and then filtering using a 10 to 20 µm filter. The resulting filtrate was spray-dried in a spray dryer to obtain 40 g of each bark extract.

The bark extracts are hereinafter indicated as *Acacia* Hot Water Extracts Nos. 1 to 5, respectively.

Production Example 3

*Acacia* Bark Extract

*Acacia* bark of the present invention was dried to a moisture content of 20% or less and after pulverizing the dried bark in a hammer mill to a powder having a particle diameter of 1.6 mm or less, five times the amount of ethanol were added to 100 g of the dried pulverized bark followed by extraction for 15 minutes while refluxing after boiling, and then filtering using a 10 to 20 µm filter. After evaporating the ethanol from the resulting filtrate, the concentrate was spray-dried in a closed spray dryer to obtain 40 g of bark extract (to be indicated hereinafter in the manner of *Acacia* Ethanol Extract No. 1).

*Acacia* Ethanol Extracts Nos. 1 to 5 were obtained in the same manner.

Production Example 4

*Acacia* Bark Extract

Three times the amount of ethanol were added to 10 g of the *acacia* hot water extract obtained in Production Example 2 followed by extraction for 15 minutes while refluxing after boiling, and then filtering using a 10 to 20 µm filter. The ethanol was evaporated from the resulting filtrate, water was added thereto, and then freeze-dried to obtain 9 g of extract (to be indicated hereinafter in the manner of *Acacia* Hot Water Extract Ethanol Fraction No. 1).

*Acacia* Hot Water Extract Ethanol fractions Nos. 1 to 5 were obtained in the same manner.

Test Example 1

Growth Inhibitory Effects During In Vitro Culturing of Tumor Cells (1) Preparation of Test Samples 2 mL of distilled water were added to 200 mg of *Acacia* Hot Water Extract No. 1 described in Production Example 2 followed by extraction for 10 minutes at 100° C. The extract was filtered (Millipore filter, pore diameter: 0.45 µm) and the filtrate was diluted 10-fold and 100-fold with 10% FCS-RPMI 1640 to prepare test samples in which the concentrations of *Acacia* Hot Water Extract No. 1 were 10 mg/mL and 1 mg/mL, respectively (the concentration was indicated as the raw material equivalent).

In addition, 2 mg of mitomycin C was diluted with 10% FCS-RPMI 1640 to prepare a 50 μg/mL solution for use as an effective control.

(2) Materials and Methods

Mouse leukemia cells YAC-1 (provided by Riken Cell Bank) were subcultured, and cells obtained on day 4 of subculturing were suspended in 10% FCS-RPMI 1640 at $1 \times 10^6$ cells/mL.

950 μL of the above YAC-1 cells ($1 \times 10^6$ cells/mL) were injected into each well of a 24-well plate followed by addition of 50 μL of the test samples prepared above, agitating and culturing for 3 days at 37° C. Following culturing, cell counts and survival rates were measured to determine the live cell counts.

(3) Results

Figure 1:
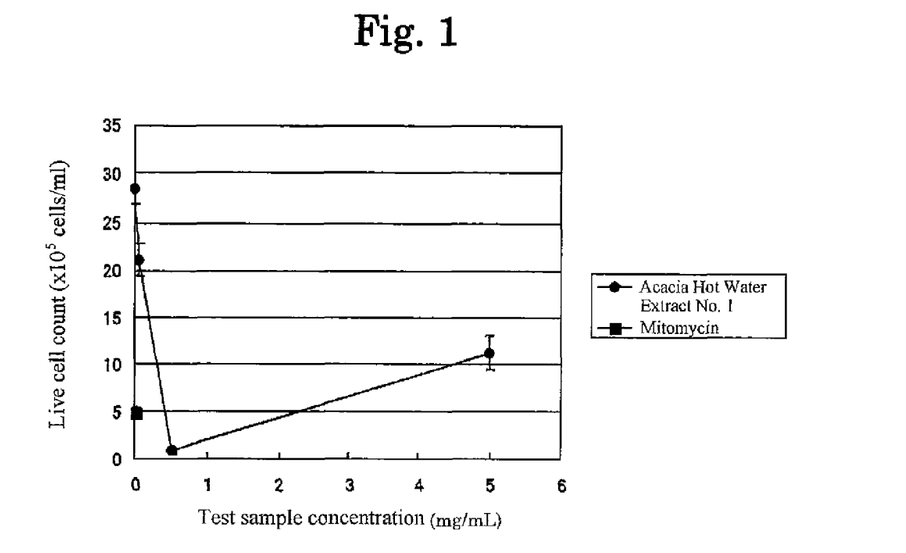
FIG. 1 is a graph showing changes in live cell counts of YAC-1 cells.

When test samples of *Acacia* Hot Water Extract No. 1 were added, the growth of YAC-1 cells was inhibited, and at a concentration of 0.5 mg/ml in particular, YAC-1 cell growth inhibitory action was demonstrated to be greater than that at a concentration of 5.0 mg/mL or that of mitomycin C (concentration: 2.5 μg/mL) (FIG. 1).

Test Example 2

Tumor Growth Inhibition Test in Mice (1) Test Method

The required weighed amounts of *Acacia* Hot Water Extract No. 1 described in Production Example 2 were dispersed in water at 60° C. to prepare test drinks 1, 2 and 3 containing *Acacia* Hot Water Extract No. 1 at 7.8 mg/mL, 15.6 mg/mL and 31.3 mg/mL, respectively.

The required weighed amounts of *Acacia* Hot Water Extract No. 1 described in Production Example 2 were mixed with commercially available feed to prepare test feeds 2 and 3 containing *Acacia* Hot Water Extract No. 1 at 15.6 mg/g and 31.3 mg/g, respectively.

Female C3H/HeN mice were assigned to a Control 1 group, Test 1 group, Test 2 group, Test 3 group and Positive Control group as shown in the table below.

TABLE 1

| | Grouping | | | | |
|---|---|---|---|---|---|
| | Days 1 to 6 of Transplantation | | | Days 7 to 28 of Transplantation | |
| Group | No. of animals | Drinking water and feed or administered substance | Group | No. of animals | Drinking water and feed or administered substance |
| Control 1 group | 10 | Tap water + control feed | Control 1 group | 10 | Tap water + control feed |
| Test 1 group | 10 | Test drink 1 + control feed | Test 1 group | 10 | Test drink 1 + control feed |
| Test 2 group | 10 | Test drink 2 + control feed | Control 2 group | 4* | Tap water + control feed |
| | | | Test 2a group | 5 | Tap water + test feed 2 |
| Test 3 group | 10 | Test drink 3 + control feed | Control 3 group | 5 | Tap water + control feed |
| | | | Test 3a group | 5 | Tap water + test feed 3 |
| Positive Control group | 5 | Tap water + control feed | Positive Control group | 5 | Tap water + control feed + lentinan |

*Four animals were used since one of the animals died prior to day 4 of transplantation.

Figure 2:
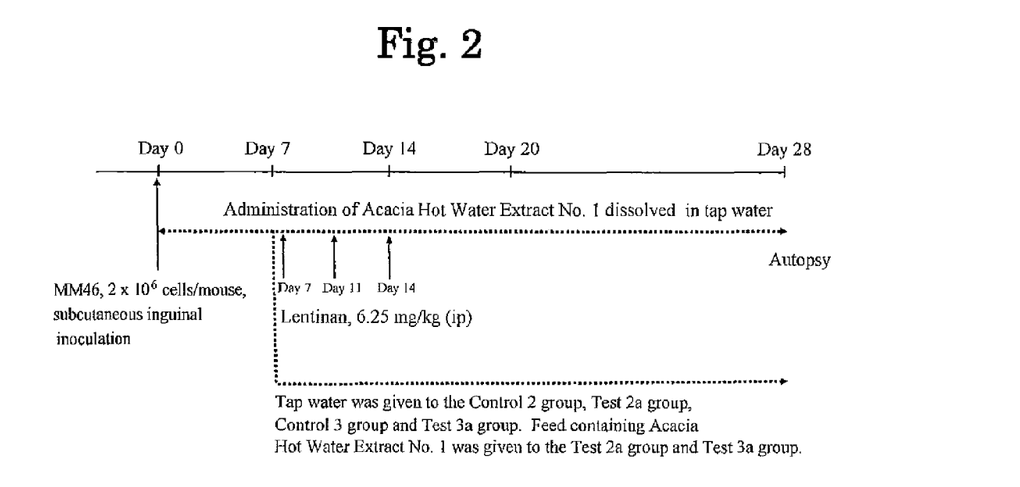
FIG. 2 is a drawing showing the time schedule of a tumor growth inhibition test in mice.

The test was carried out according to the time schedule shown in FIG. 2.

First, $2×10^6$ mouse tumor MM46 breast cancer cells were transplanted subcutaneously into the inguinal region of the mice grouped as indicated above according to the method described in Abe, S. et al., Gann 73, 91-96 (1982) and Ohasi, K. et al., Yakugaku Zasshi 113, 396-399 (1993).

Tap water was given to the Control 1 group while Test Drinks 1 to 3 were given to the Test 1 to Test 3 groups, respectively, as drinking water, starting on the day of tumor transplantation. In addition, tap water was given to the Positive Control group, and this group was also intraperitoneally administered 6.25 mg/kg of lentinan on days 7, 11 and 14 following tumor transplantation.

Water consumption in the Test 2 group and Test 3 group was 0.2 mL/day, which was much lower than that of the other groups at 4 to 6 mL/day, and the animals of the former groups also exhibited prominent weight loss. Consequently, Test Drink 2 and Test Drink 3 were replaced with tap water on day 7 of tumor transplantation. In addition, five mice each of the Test 2 group were reassigned to a Control 2 group and a Test 2a group, while five mice each of the Test 3 group were reassigned to a Control 3 group and a Test 3a group. Animals of the Control 2 group and Control 3 group were continued to be fed the control feed. The Test 2a group and Test 3a group were fed Test Feed 2 and Test Feed 3, respectively, instead of the control feed.

Growth of the tumor transplanted subcutaneously into the inguinal regions of the mice was observed by palpation for 4 weeks every 3 or 4 days, and tumor diameter was also measured. In addition, survival times (days) and body weights were also measured. The tumors were excised and their wet weights were measured following completion of the test.

(2) Test Results

Figure 3:
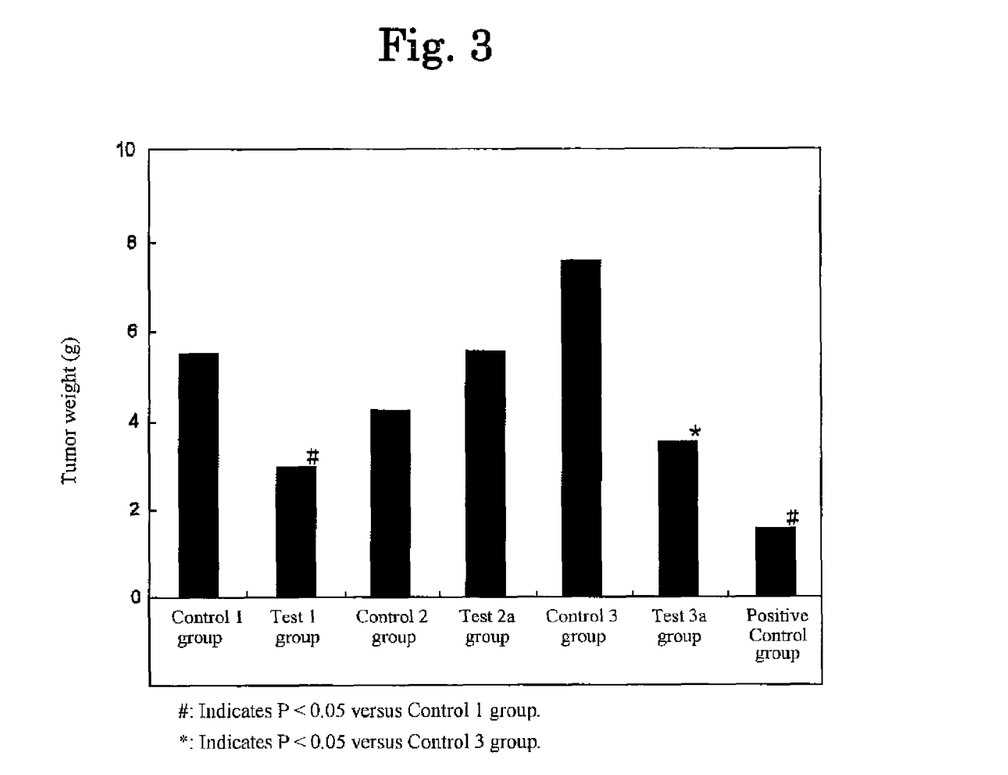
FIG. 3 is a graph showing average tumor weights on day 28 after transplantation in mice.

The results are shown in Table 2 and FIG. 3. Furthermore, the Student's t-test was used for statistical testing.

TABLE 2

Action on Average Tumor Diameter

| Dose group | Day 14 after transplantation | Day 28 after transplantation |
|---|---|---|
| Control 1 group | 13.1 ± 3.93 | 23.8 ± 5.29 |
| Test 1 group | 10.5 ± 4.03 (19.8)[a] | 19.6 ± 3.92 (17.6)[a] |
| Control 2 group | 12.2 ± 0.84 | 22.0 ± 2.74 |
| Test 2a group | 13.0 ± 1.15 (−6.56)[b] | 24.8 ± 1.50 (−12.7)[b] |
| Control 3 group | 13.0 ± 1.73 | 28.2 ± 1.30 |
| Test 3a group | 10.2 ± 1.79 (21.5)[c] | 20.6 ± 2.97* (27.0)[c] |
| Positive Control group | 7.4 ± 6.58 (43.5)[a] | 14.0 ± 6.12 (41.2)[a] |

Units: mm
[a]Indicates reduction rate (%) versus Control 1 group.
[b]Indicates reduction rate (%) versus Control 2 group.
[c]Indicates reduction rate (%) versus Control 3 group.
*Indicates P < 0.05 versus Control 3 group.

On the basis of the above, the *acacia* bark was determined to inhibit growth of leukemia cells and breast cancer, and was observed to have an anti-tumor activity.

In the Test 1 group and Test 3a group, tumors were inhibited starting on day 14 after transplantation, and the anti-tumor action of the *acacia* bark was observed to appear rapidly.

In the Test 2 group and Test 3 group, although decreases in water consumption were observed, this was thought to be due to the strong bitter taste of the test drinks containing high concentrations of the *acacia* bark. When the test drinks were replaced with tap water and instead the test feeds were given, body weights were observed to recover, thus indicating that the weight loss was not attributable to toxicity of the *acacia* bark.

Test Example 3

Mutagenicity Test

A mutagenicity test was conducted in compliance with the Ministry of Health, Labor and Welfare Notification No. 77 (Sep. 1, 1988). As a result of testing with test substance (*Acacia* Hot Water Extracts Nos. 1 to 5 of Production Example 2) at doses of 156 to 5,000 μg/plate, there were no increases in the numbers of revertant colonies for any of the bacterial strains.

Test Example 4

Micronucleus Test

The presence of the ability to induce micronuclei was investigated in vivo in accordance with ordinary methods. *Acacia* Hot Water Extract No. 1 was orally administered twice at 24-hour intervals at daily doses of 2,000, 1,000 and 500 mg/kg to male ICR mice followed by the preparation of micronucleus specimens 24 hours after the final dosing.

*Acacia* Hot Water Extract No. 1 did not demonstrate positive results at any of the dose levels. In addition, there were no constant fluctuations in the simultaneously observed ratio of total polychromatic erythrocytes to total erythrocytes, and inhibition of erythrocyte proliferation was not observed in comparisons with a negative control group.

Test Example 5

Mouse Acute Toxicity Study (Oral Administration)

An acute oral dose toxicity study was conducted using male and female ICR mice in compliance with OECD (Guidelines for the Testing of Chemicals, 401, 1987). As a result, the $LD_{50}$ value of *Acacia* Hot Water Extract No. 1 was 4,468 mg/kg among males and 3,594 mg/kg among females.

Similar results were obtained in the above study for *Acacia* Hot Water Extracts Nos. 2 to 5 of Production Example 2.

Test Example 6

Rat Repeated Dose Toxicity Study (Oral Administration)

A 13-week repeated dose toxicity study was conducted using rats in accordance with ordinary methods. Mixed feed containing 0.5, 1.5 and 5.0% of *Acacia* Hot Water Extract No. 1 was fed to male and female Slc:SD rats.

As a result, none of the rats died or demonstrated abnormalities in examinations, including general condition.

Test Example 7

Human Single Dose Study

Five healthy adult males age 32 to 43 years were given 1500 mg of *Acacia* Hot Water Extract No. 1 (12 tablets of Formulation Example 4 described below). Although general examinations, hematology tests, blood biochemistry tests and urinalyses were performed on the subjects before ingestion, 3 hours after ingestion, 8 hours after ingestion, 24 hours after ingestion and 1 week after ingestion, there were no clinically significant fluctuations in test values. There were also no adverse events attributable to the tablets.

Test Example 8

Human 4-Week Continuous Dosing Study

Twenty-five healthy adult males age 23 to 44 years were given *Acacia* Hot Water Extract No. 1 of Formulation Example 4 described below at 750 mg/day (6 tablets of Formulation Example 4) and 1000 mg/day (8 tablets of Formulation Example 4) for 4 weeks each.

General examinations, hematology tests and urinalyses were performed on the subjects of each group before ingestion, 2 weeks after ingestion, 4 weeks after ingestion and 2 weeks following completion of ingestion. There were no clinically significant fluctuations in test values. There were also no adverse events.

Formulation Example 1

Preparation of Internal Medication

An internal medication having the composition indicated below was prepared using the *acacia* bark Hot Water Extract Ethanol Fraction of Production Example 4.

| | |
|---|---|
| Extract fraction of Production Example 4 | 1.0 (wt %) |
| Lactose | 30.0 |
| Cornstarch | 60.0 |
| Crystalline cellulose | 8.0 |
| Polyvinyl pyrrolidone | 1.0 |
| Total | 100.0 |

Formulation Example 2

Preparation of Pet Food

A pet food having the composition indicated below was prepared using the *acacia* bark Hot Water Extract of Production Example 2.

| | |
|---|---|
| Extract of Production Example 2 | 1.0 (wt %) |
| Oatmeal | 88.0 |
| Starch | 5.0 |
| Salt | 2.5 |
| Whole egg | 3.0 |
| Flavoring | 0.5 |
| Total | 100.0 |

Formulation Example 3

Preparation of Tablets (Confections)

Tablets (confections) having the composition indicated below were prepared using the *acacia* bark Hot Water Extract Ethanol Fraction of Production Example 4.

| | |
|---|---|
| Extract fraction of Production Example 4 | 1.0 (wt %) |
| Citric acid | 1.0 |
| Powdered skim milk | 15.0 |
| Sucrose ester | 1.0 |
| Flavoring | 0.5 |
| Powdered sugar | 20.0 |
| Lactose | 61.5 |
| Total | 100.0 |

Formulation Example 4

Preparation of Tablets

Tablets having the composition indicated below were prepared using *Acacia* Bark Hot Water Extract No. 1 of Production Example 2.

| | |
|---|---|
| *Acacia* Bark Hot Water Extract No. 1 of Production Example 2 | 125 (mg) |
| Sucrose ester | 9 |
| Lactose | 166 |
| Total | 300 |

INDUSTRIAL APPLICABILITY

According to the present invention, a composition for preventing and/or treating a tumor can be obtained.

More specifically, the composition of the present invention is useful for preventing and/or treating various types of benign or malignant tumors.

The composition can be used as a medicine, a guasi-drug or a cosmetic, or a food or an animal feed material such as a health food, a health supplement food, a food for specified health use or a nutritional supplement food.

The invention claimed is:

1. A method of treating leukemia comprising administering to a subject in need thereof a composition consisting of:
   (a) a hot water extract(s) of *Acacia* bark, wherein the *Acacia* bark comprises at least one bark selected from *Acacia mearnsii* De Wild., *Acacia mangium* Willd., *Acacia dealbata* Link, *Acacia decurrens* Willd, and *Acacia pycnantha* Benth; and
   (b) optionally, at least one of black vinegar, onion extract, yacon, a pharmaceutical vehicle, a sweetener, a flavoring, a thickener, a fragrance, a pigment, and an emulsifier.

2. The method of claim 1, wherein the *Acacia* bark comprises at least one bark selected from the group consisting of *Acacia mearnsii* De Wild. and *Acacia mangium* Willd.

3. The method of claim 1, wherein the *Acacia* bark is a bark of *Acacia mearnsii* De Wild.

4. The method of claim 1, wherein the hot water extract(s) of acacia bark is an acacia bark polyphenol(s).

5. The method of claim 1, wherein the composition is a food.

6. The method of claim 4, wherein the *acacia* bark polyphenol(s) is a condensed tannin(s).

7. The method of claim 4, wherein the *acacia* bark polyphenol(s) is administered orally at 0.001 to 1 g per kg of body weight per day in terms of the amount of active ingredient.

8. The method of claim 6, wherein the condensed tannin(s) has a molecular weight(s) of 500 to 3000.

9. The method of claim 6, wherein the condensed tannin(s) is a polymer(s) of flavanols having flavan-3-ol as a basic skeleton.

* * * * *